United States Patent
Chiche et al.

(10) Patent No.: US 9,879,325 B2
(45) Date of Patent: Jan. 30, 2018

(54) METHOD FOR PREDICTING THE RESPONSIVENESS A PATIENT TO A TREATMENT WITH AN ANTI-CD20 ANTIBODY

(71) Applicants: ASSISTANCE PUBLIQUE—HÔPITAUX DE PARIS, Paris (FR); UNIVERSITÉ PARIS DIDEROT (PARIS VII), Paris (FR); UNIVERSITÉ DE NICE—SOPHIA ANTIPOLIS, Nice (FR); INSTITUT NATIONAL DE LA SANTÉ ET DE LA RECHERCHE MÉDICALE, Paris (FR)

(72) Inventors: Johanna Chiche, Nice (FR); Catherine Thieblemont, Paris (FR); Jean-Ehrland Ricci, Nice (FR)

(73) Assignees: ASSISTANCE PUBLIQUE—HÔPITAUX DE PARIS, Paris (FR); UNIVERSITÉ PARIS DIDEROT (PARIS VII), Paris (FR); UNIVERSITÉ DE NICE—SOPHIA ANTIPOLIS, Nice (FR); INSTITUT NATIONAL DE LA SANTÉ ET DE LA RECHERCHE MÉDICALE, Paris (FR)

(*) Notice: Subject to any disclaimer, the term of this patent is extended or adjusted under 35 U.S.C. 154(b) by 0 days.

(21) Appl. No.: 15/121,864

(22) PCT Filed: Feb. 27, 2015

(86) PCT No.: PCT/EP2015/054209
§ 371 (c)(1),
(2) Date: Aug. 26, 2016

(87) PCT Pub. No.: WO2015/132163
PCT Pub. Date: Sep. 11, 2015

(65) Prior Publication Data
US 2017/0073762 A1   Mar. 16, 2017

(30) Foreign Application Priority Data
Mar. 3, 2014 (EP) .................. 14305297

(51) Int. Cl.
A61K 39/395 (2006.01)
C07K 16/30 (2006.01)
G01N 33/53 (2006.01)
C12Q 1/68 (2006.01)
G01N 33/50 (2006.01)
G01N 33/574 (2006.01)
C07K 16/28 (2006.01)

(52) U.S. Cl.
CPC ........ *C12Q 1/6886* (2013.01); *C07K 16/2887* (2013.01); *C07K 16/3061* (2013.01); *G01N 33/5052* (2013.01); *G01N 33/57426* (2013.01); *C07K 2317/24* (2013.01); *C12Q 2600/106* (2013.01); *C12Q 2600/158* (2013.01); *G01N 2333/90203* (2013.01); *G01N 2800/52* (2013.01)

(58) Field of Classification Search
None
See application file for complete search history.

(56) References Cited

FOREIGN PATENT DOCUMENTS

WO   2012/118750 A2   9/2012
WO   2013/020690 A1   2/2013

OTHER PUBLICATIONS

Wang et al., "The Expression of Glyceraldehyde-3-Phosphate Dehydrogenase Associated Cell Cycle (GACC) Genes Correlates with Cancer Stage and Poor Survival in Patients with Solid Tumors" PLOS ONE, 8:1-10, 2013.*
Tomita, "Genetic and Epigenetic Modulation of CD20 Expression in B-Cell Malignancies: Molecular Mechanisms and Significance to Rituximab Resistance", J Clin Exp Hematop 56(2):89-99, 2016.*
Jiang et al., "Proteomic analysis of mitochondria in Raji cells following exposure to radiation: implications for radiotherapy response", Protein and Peptide Letters 2009, 2009, pp. 1350-1359, vol. 16, No. 11.
Cang et al., "Novel CD20 monoclonal antibodies for lymphoma therapy", Journal of Hematology & Oncology, Oct. 11, 2012, p. 64, vol. 5, No. 1, Biomed Central, London, UK.
Tsai et al., "Regulation of CD20 in Rituximab-Resistant Cell Lines and B-Cell Non-Hodgkin Lymphoma", Clinical Cancer Research, Jan. 6, 2012, pp. 1039-1050, vol. 18, No. 4.

* cited by examiner

*Primary Examiner* — Ron Schwadron
(74) *Attorney, Agent, or Firm* — Whitham, Curtis & Cook, P.C.

(57) ABSTRACT

The present invention relates to a method for predicting the responsiveness of a patient to a treatment with an anti-CD20 antibody, said method comprising measuring the level of glyceraldehyde-3-phosphate dehydrogenase (GAPDH) expression in B cells obtained from said patient.

3 Claims, 4 Drawing Sheets

METHOD FOR PREDICTING THE RESPONSIVENESS A PATIENT TO A TREATMENT WITH AN ANTI-CD20 ANTIBODY

FIELD OF THE INVENTION

The present invention relates to a method for predicting the responsiveness of a patient to a treatment with an anti-CD20 antibody.

BACKGROUND OF THE INVENTION

Antibodies to CD20 have confirmed the hypothesis that monoclonal reagents can be given in vivo to alleviate human diseases. The targeting of CD20 on normal, malignant and auto-immune B-lymphocytes by rituximab has demonstrated substantial benefits for patients with a variety of B-cell lymphomas, as well as some with autoimmune disorders. There has been a notable increase in the survival rates from B-cell lymphoma in the decade since anti-CD20 therapy was introduced.

Monoclonal antibody (mAb) therapy with the anti-CD20 mAb rituximab represents one of the most important advances in the treatment of lymphoproliferative disorders in the last 30 years. Prior to its introduction, there had been only modest improvement in the treatment outcome of diseases such as follicular (FL) and diffuse large B-cell lymphoma (DLBCL). However, the use of rituximab, particularly in combination with various chemotherapy/radiotherapy regimes, has significantly improved all aspects of the survival statistics for these patients. In addition, rituximab is approved, or being investigated for the treatment of many other hematologic disorders ranging from other malignancies, such as chronic lymphocytic leukemia (CLL), to autoimmune disorders, such as immune and thrombotic thrombocytopenic purpura and rheumatoid arthritis (Lim et al. Haematologica. 2010; 95(1): 135-143).

Despite the success of anti-CD20 therapy, resistance occurs in about half of the patients, resulting in non-response to treatment or early relapse of the original disease.

Number of cells expressing CD20 in addition to CD20 cell surface density has been clearly shown to determine anti-CD20 mAb sensitivity at an early stage (Tsai et al., 2012). Therefore investigating the regulation of CD20 expression is a prime interest.

Molecular discrimination of responders versus non responders to anti-CD20 antibody becomes a major clinical interest, and there is a permanent need in the art for prognostic biomarkers that could assist physicians in providing patients optimized care management with anti-CD20 antibody.

SUMMARY OF THE INVENTION

The present invention relates to a method for predicting the responsiveness of a patient to a treatment with an anti-CD20 antibody, said method comprising measuring the level of glyceraldehyde-3-phosphate dehydrogenase (GAPDH) expression in B-cells obtained from said patient.

A high level of GAPDH expression is predictive of a response to an anti-CD20 antibody treatment.

Patients with high GAPDH expression, have a higher CD20 expression and a better response to anti-CD20 based therapy.

DETAILED DESCRIPTION OF THE INVENTION

The expression "predicting the responsiveness of a patient to a treatment with an anti-CD20 antibody", should be understood broadly, it encompasses a prediction made before starting any treatment with an anti-CD20 antibody and prediction made during a treatment with an anti-CD20 antibody.

The method of the present invention allows the detection of a resistance to an anti-CD20 therapy.

Thus, the present invention also relates to a method for detecting anti-CD20 antibody resistance of a patient undergoing a treatment with an anti-CD20 antibody, said method comprising measuring the level of glyceraldehyde-3-phosphate dehydrogenase (GAPDH) expression in B-cells obtained from said patient.

A low level of GAPDH expression is predictive of a non-response to an anti-CD20 antibody treatment.

Glyceraldehyde-3-phosphate dehydrogenate (GAPDH) catalyzes the reaction of glyceraldehyde-3-phosphate $(G3P)+NAD^{+}+Pi$ into 1,3 diphosphoglycerate$+NADH+H^{+}$. GAPDH is a key enzyme of the glycolytic pathway.

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments or derivatives. Antibody fragments include but are not limited to Fv, Fab, F(ab')2, Fab', dsFv, scFv, sc(Fv)2 and diabodies.

Preferably, said anti-CD20 antibody is a monoclonal antibody.

CD20-targeted therapy is well known see for example for review van Meerten et al. Neth J Med. 2009 July-August; 67(7):251-9, Lim et al. Haematologica. 2010; 95(1): 135-143) and Cang et al. Journal of Hematology & Oncology 2012, 5:64.

The term "anti-CD20 antibody" refers to an antibody directed against the CD20 antigen. The CD20 antigen is expressed on B lymphocytes.

Examples of anti-CD20 antibodies include but are not limited to rituximab, ibritumomab, ofatumumab, ocrelizumab, PRO131921, veltuzumab, AME-133v, tositumomab, GA-101.

Preferably, said anti-CD20 antibody is rituximab.

The term "patient" refers to any subject (preferably human) afflicted with a disease likely to benefit from a treatment with an anti-CD20 antibody.

Said disease is preferably selected from the diseases that are associated with a proliferation or an over activation of B cells. The diseases may be selected from the group consisting of non Hodgkin's B cell lymphoma, such as for example follicular lymphoma (FL), Burkitt lymphoma and diffuse large B-cell lymphoma (DLBCL), Waldenström's macroglobulinemia, leukemia, such as chronic lymphocytic leukemia (CLL); and auto-immune diseases such as rheumatoid arthritis, idiopathic autoimmune hemolytic anemia, Pure red cell aplasia, idiopathic thrombocytopenic purpura, Evans syndrome, vasculitis, multiple sclerosis, bullous skin disorders (for example pemphigus, pemphigoid), type 1 diabetes mellitus, Sjogren's syndrome, Devic's disease, Wegener's granulomatosis, Microscopic polyangiitis and systemic lupus erythematosus.

Preferably the patient is a B-cell lymphoma patient, more preferably a diffuse large B-cell lymphoma patient.

Diffuse large-B cell lymphoma (DLBCL) are the most common type of non-Hodgkin's (NH) lymphomas in adults (Alizadeh et al., 2000). Despite an evident survival benefit when DLBCL are treated with the anti-CD20 monoclonal antibody rituximab (R) in addition to the standard multi-agent anthracyclines containing chemotherapies cyclophosphamide, hydroxydaunorubicin, oncovin, prednisone (CHOP), a significant proportion of patients (☐40%) still demonstrate a poor clinical outcome as they experience treatment failure defined as no response to rituximab-combined chemotherapy in the first-line setting or partial response or relapse after initial chemotherapy (Thieblemont and Gisselbrecht, 2009). Number of cells expressing CD20 in addition to CD20 cell surface density has been clearly shown to determine rituximab sensitivity at an early stage (Tsai et al., 2012).

The level of GAPDH expression in B-cells obtained from the patient may be determined using any technique suitable for detecting GAPDH levels in cells.

Typically, the level of GAPDH expression may be determined by quantitative PCR (qPCR), or immunohistochemistry or by measuring the GAPDH enzymatic activity.

Typically the B cells are obtained from a biopsy, preferably a lymph node biopsy or from a blood sample.

Flow cytometry may also be used to obtain B cells.

An example of method for measuring the level of GAPDH expression in B cells is:

Cells are permeabilized and fixed using the BD Cytofix/cytoperm solution (BD Biosciences) and incubated at 4° C. for 20 min. The cells are then washed in saponin containing buffer (BD Perm/Wash) and resuspended in the same buffer containing anti-GAPDH antibody (Abcam ab9485; dilution 1/100) and incubated for 30 min at 4° C. The cells are washed twice with the saponin-containing buffer and incubated with a Allophycocyanin (APC)-coupled anti-Rabbit antibody (dilution 1/100) for 30 min at 4° C. in the same buffer. After washing twice in the saponin-containing buffer, the cells are resuspended in PBS/2% FCS and analyzed by flow cytometry.

The method of the invention may further comprise a step of comparing the GAPDH expression level with reference values obtained from responder and non-responder group of patients, wherein detecting differential in the GAPDH expression level with the reference values is indicative whether the patient will be a responder or not to the treatment with an anti-CD20 antibody.

A "responder" patient refers to a patient who shows a clinically significant relief in the disease when treated with an anti-CD20 antibody.

After being tested for responsiveness to a treatment with an anti-CD20 antibody, the patients may be prescribed with said anti-CD20 antibody or if the anti-CD20 antibody treatment already started, the anti-CD20 treatment may be continued.

An embodiment of the invention relates to a method for treating with anti-CD20 antibody a patient in need thereof, wherein said method comprises the following steps:

a) identifying if a patient is responsive to treatment with an anti-CD20 antibody with the method for predicting the responsiveness according to the invention; and
b) treating with an anti-CD20 antibody the responder patient identified.

The invention also relates to an anti-CD20 antibody for use in a method for treating a patient in need thereof, wherein said method comprises the following steps:

a) identifying if a patient is responsive to treatment with an anti-CD20 antibody with the method for predicting the responsiveness according to the invention; and
b) treating with an anti-CD20 antibody the responder patient identified.

Thus, the invention relates to an anti-CD20 antibody for use in a method for treating a patient in need thereof, wherein said patient has been identified as responsive with the method for predicting the responsiveness according to the invention.

The method may be performed on patients before starting any anti-CD20 antibody treatment, the method allows the identification of patients that will be responsive to the anti-CD20 antibody treatment.

Alternatively, the method may be performed on patients already undergoing an anti-CD20 antibody treatment, the method allows the identification of patients that are still responsive to the anti-CD20 antibody treatment.

If the patients are identified as resistant i.e. not responsive anymore to the anti-CD20 antibody treatment, the anti-CD20 antibody treatment is discontinued or adapted in order to increase the CD20 expression in B-cells.

The invention will be further illustrated by the following example and figure. However, this example and figure should not be interpreted in any way as limiting the scope of the present invention.

EXAMPLES

Example 1

Summary

Figure 1:
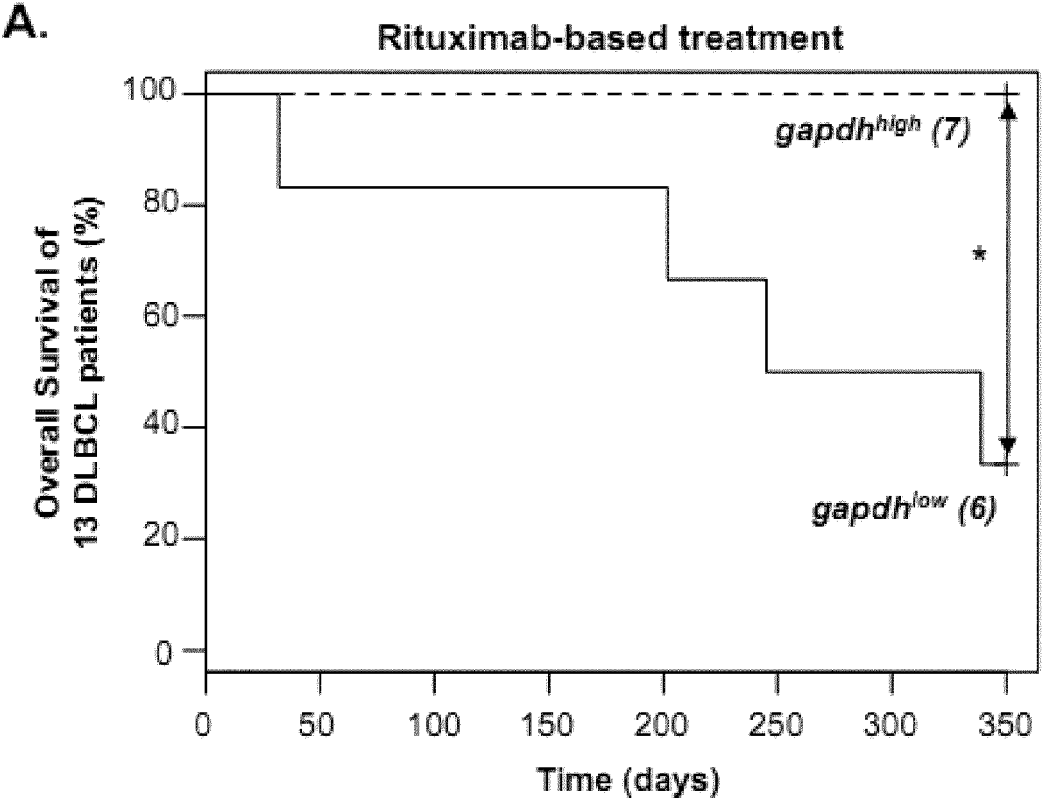
FIG. 1: GAPDH expression increases CD20 expression and is a favorable prognosis factor for DLBCL patients treated with anti-CD20 based therapy. A. Kaplan-Meier survival analysis for overall survival of DLBCL patients classified according to gapdh mRNA levels of expression.

Despite their functions in metabolism, the role of glycolytic enzymes in cancers remains elusive. Here we show that glyceraldehyde-3-phosphate dehydrogenase (GAPDH) but no other glycolytic enzyme tested, increased lymphoma aggressiveness and vascularization. Mechanistically, GAPDH activates NF-κB via its binding to the TNF-receptor-associated factor-2 (TRAF2) resulting in an increase in hif-1α transcription and in an up-regulation of CD20 expression. Among the diffuse large B cell lymphoma (DLBCL)

patients tested, the one with higher GAPDH levels presented more CD20 expression and had a better outcome upon rituximab treatment. Thus GAPDH participates in a positive feedback loop that promotes NF-κB/HIF-1 activation favoring CD20 expression and may therefore represent a favorable prognosis factor for DLBCL patients treated with anti-CD20 therapy.

Introduction

The present study was undertaken to investigate if specific glycolytic enzymes could play a role in cancer development and response to chemotherapy. It was mainly performed using the Eμ-Myc transgenic mouse model, in which all animals spontaneously develop clonal pre-B or B-cell lymphoma that resemble human NH B lymphomas (Harris et al., 1988), highly glycolytic and aggressive types of tumors. We determined that GAPDH but no other glycolytic enzymes tested contributes to an increase in lymphoma growth and vascularization. Mechanistic investigations revealed that GAPDH regulation of HIF-1α is mediated by NF-κB activation, a process driven by GAPDH interaction with TRAF2. Importantly, GAPDH-mediated control of NF-κB/HIF-1α axis in hypoxia lead to an increase in CD20 expression, allowing high GAPDH-expressing DLBCL patients to present a better survival upon Rituximab-based treatment.

Results

Increase of GAPDH Expression Accelerates cMyc-Driven Lymphomagenesis.

Eμ-Myc mice are developing very aggressive lymphoma and die a few months after birth. By monitoring overall life span of Eμ-Myc mice we observed that most of them could be regrouped in two groups: the one developing highly aggressive lymphomas ("high", median survival below 11 weeks, n=15) as opposed to the one developing lower aggressive lymphoma ("low", median survival over 20 weeks, n=10). In agreement with the Warburg effect, we observed that the highly aggressive lymphomas are more glycolytic than the lower aggressive ones, as they are producing more lactate in vivo. Surprisingly when we monitored the expression of several glycolytic enzymes, we observed that only one, the GAPDH, was significantly overexpressed (two-fold) in the "highly" aggressive group compared to the "low" group. This increase in GAPDH protein levels correlated closely with the increase in GAPDH specific activity in the lymph nodes of the "high" group.

To assess the role of GAPDH in lymphoma aggressiveness, primary B lymphoma cells isolated from Eμ-Myc mice were stably silenced (shgapdh) or not (shctl) for endogeneous GAPDH (see experimental procedure). While partial reduction in GAPDH expression did not impact on in vitro proliferation of Eμ-Myc cells, mice injected with Eμ-Myc-shgapdh cells survived longer than the controls and presented a decrease in the overall weight of the axillary lymph nodes. We validated upon sacrifice that lymph node tumors obtained from Eμ-Myc-shgapdh cells were indeed presenting a reduction in GAPDH expression and GAPDH specific activity compared to controls. We also verified that cells harvested from lymph node tumors had the same extend of CD19+/GFP+ cells in each group.

To further confirm the specific role of GAPDH expression on lymphoma progression we overexpressed it in primary Eμ-Myc lymphoma cells. The overexpression of GAPDH significantly accelerated the lymphoma growth and therefore decrease the lifespan of the mice compared to the control group (pMIG). As opposed to GAPDH-V5, overexpression of V5-tagged Enolase-1 (ENOL-V5, another non-limiting glycolytic enzyme) or pyruvate-kinase M2 (PKM2-V5, the last limiting enzyme of glycolysis) did not modify the lifespan of the mice compared to what obtained with control cells. The reduction of the survival upon GAPDH overexpression closely correlated with the increase in the size of the lymph nodes compared to other groups despite the same rate of proliferation in vitro in basal (normoxic) condition. Upon sacrifice, we isolated lymphoma cells from each group and verified that GAPDH-V5 expressing cells were indeed presenting an increase in GAPDH specific activity compared to the other groups. Of note, similar results were obtained using independent Eμ-Myc clones.

Upon analysis, we not only observed that the mice injected with GAPDH-V5 expressing lymphoma cells have bigger lymph nodes but in addition, those ones were more vascularized than the controls, as shown by an increase i) in hemoglobin content ii) in vascularized structures stained for endothelial CD31 marker within the lymph nodes and iii) in the mRNA of the angiogenic factor vegf-α. Interestingly, mRNA levels of the a subunit of the Hypoxia-Inducible transcription factor hif-1α were higher in GAPDH- but not in ENO- or PKM2-overexpressing lymphoma cells. To further generalize our observations we analyzed the expression of those genes in DLBCL patients by real-time qPCR. Out of the 13 DLBCL patient samples analyzed, 6 were "low" and 7 were "high" expressers of gapdh mRNA (see experimental procedures). As observed in vivo using the Eμ-Myc model, patients expressing the highest level of GAPDH are presenting high levels hif-1α and vegf-α but not hif-2α mRNA when compared to the "low" gapdh expressers.

Taken together our results suggest that GAPDH overexpression but no other glycolytic enzyme tested participate in increase lymphoma aggressiveness.

GAPDH regulates NF-κB activation through its binding to TRAF2 and leads to HIF-1α induction.

As we observed i) an increase in tumor growth and vascularization of the GAPDH overexpressing lymphomas, ii) a GAPDH-dependent increase in hif-1α and HIF-1-induced vegf-α mRNA levels, we therefore investigated the consequences of GAPDH expression on HIF-1α expression and HIF-1 activity in hypoxia. We observed in primary Eμ-Myc and in HeLa cells that GAPDH overexpression was able to increase HIF-1α expression and HIF-1 transcriptional activity after 24 hours of hypoxia. It is worth noting that the level of expression/activity of GAPDH obtained upon overexpression is consistent with a physiological overexpression of GAPDH observed after 24 hours of hypoxia. Transcriptional up-regulation of hif-1α observed in Eμ-Myc cells in vivo was confirmed in HeLa cells overpexressing GAPDH.

In addition, increase in HIF-1α expression observed upon GAPDH expression could not be obtained upon expression of PKM2 or ENOL, indicating a specificity of the effect. As demonstrated recently (Luo et al., 2011), we confirmed that PKM2 overexpression while unable to stabilize HIF-1α expression increases its activity in HeLa cells. We established in vitro that GAPDH over-expression was unable to affect cell proliferation in normoxia but allow the cells to increase glycolysis and proliferation rate by □30% in hypoxia. These results are consistent with the ability of GAPDH to activate HIF-1 in hypoxia.

We then verified in Eμ-Myc and in HeLa cells that a decrease in GAPDH levels using shRNAs was leading to a decrease in hif-1α mRNA levels, in HIF-1α protein expression and in expression of HIF-1-targeted genes in hypoxia. As a result, glycolysis and proliferation were significantly reduced in hypoxia. Interestingly, the use of non-toxic doses of a GAPDH specific inhibitor, the Koningic acid (KA), reduces GAPDH activity by □50-60% and was able to mimic the decrease in HIF-1 activity and HIF-1α expression observed with shRNA targeting GAPDH.

As NF-κB, a key regulator of hif-1α transcription, is controlled in part by Akt, and as we recently established that GAPDH could stabilize the active form of Akt (Jacquin et al., 2013), we investigated NF-κB activation upon GAPDH expression. For that matter, Eμ-Myc or HeLa cells stably expressing (GAPDH-V5) or not (pMIG) GAPDH were cultured in normoxia or in hypoxia for 24 hours. We not only confirmed that in hypoxia GAPDH was also able to increase Aid phosphorylation but also to increase Ser32-36 phosphorylation of IκBα in normoxia and in hypoxia. As a result, transcriptional activity of NF-κB was either increased when GAPDH was overexpressed or decreased when GAPDH was silenced. While GAPDH expression stabilizes phospho-Akt, inhibition of Akt activation using a specific inhibitor of Akt did not prevent IκBα phosphorylation. Therefore GAPDH can induce an activation of the NF-κB pathway in an Akt independent manner.

To further investigate the contribution of NF-κB in the regulation of HIF-1α by GAPDH, we used a dominant negative form of IκBα (IκBαS32-36A). Expression of IκBαS32-36A collapsed NF-κB activity and HIF-1α protein expression, indicating that GAPDH-dependent activation of NF-κB is required for GAPDH-mediated regulation of HIF-1α. Interestingly this observation was confirmed in DLBCL samples from patients as the "high" gapdh expressers are presenting an increased expression of nfkbia mRNA, a specific target of NF-κB, reflecting NFkB activation (Bottero et al., 2003).

To demonstrate that classical NF-κB pathway was indeed activated by GAPDH, gapdh-silenced HeLa cells were stimulated with TNFα in hypoxia. As a result, gapdh-silenced cells failed to fully enhance NF-κB activity, compared to control cells stimulated with TNFα. We further confirmed the role of GAPDH on NF-κB activation using the Burkitt cell line RAJI using Electromobility Shift Analysis (EMSA) assay. While TNFα stimulation or hypoxic incubation enhance NF-κB binding to its consensus sequence, GAPDH inhibition using KA reduced its binding in hypoxia and prevented NF-κB transcriptional activity in hypoxic HeLa cells.

It was recently demonstrated that upon bacterial infection, inflammatory response of the host cell is suppressed, a process that involves disruption of GAPDH-TRAF2 interaction (Gao et al., 2013). Consequently, we investigated GAPDH-TRAF2 binding in Eμ-Myc and HeLa cells and evidenced that GAPDH could be co-immunprecipitated with TRAF2 when cells are cultured in hypoxia. Specific and partial inhibition of GAPDH with KA in hypoxia decreases NF-κB activity as a result of a loss of GAPDH-TRAF2 interaction. We further tested this interaction in vivo. For that matter Eμ-Myc bearing mice were treated once with PBS or with the covalent inhibitor koningic acid (i.p) and GAPDH/TRAF2 interaction was investigated by co-immunoprecipation in tissues, 24 hours after treatment. Very interestingly we could confirm that GAPDH can bind TRAF2 in vivo and that an efficient dose of KA (5 mg/kg) but not an inactive dose of KA (0.5 mg/kg) reduced the interaction observed between those endogenous proteins. We then confirmed in vivo that GAPDH inhibition (using KA 5 mg/kg) reduced hif-1α mRNA in vivo underling the link between GAPDH, NF—κB and HIF-1α expression.

To further understand the underling link between GAPDH—NF—κB and lymphoma aggressiveness, we used a GAPDH double mutant (DM, GAPDH C152S and H179F) that is unable to sustain the glycolytic function of the enzyme (Colell et al., 2007). We verified that DM failed to bind TRAF2, to activate NF-κB and to elevate HIF-1α expression in hypoxic Eμ-Myc compared to WT GAPDH, suggesting that the catalytic site of the enzyme is playing a role in the effect.

Consequently, DM-overexpressing Eμ-Myc cells could not increase lymphoma progression in vivo as opposed to GAPDH overexpression. Of note, no significant difference could be observed between GAPDH and Bcl-xL expressing Eμ-Myc cells (Bcl-xL being considered as an inducer of a very aggressive lymphoma). Finally GAPDH but not DM nor Bcl-xL expression was leading to an increase in total VEGF secretion, as a consequence of NF-κB and HIF-1 activation. We verified upon sacrifice of the mice that only GAPDH-expressing Eμ-Myc cells were presenting more GAPDH activity and that the expression of the indicated protein could be observed in the lymph nodes of the injected mice.

Our finding indicate that GAPDH, as opposed to other glycolytic enzyme tested, can increase lymphoma growth and vascularization in vivo and that this effect was mediated at least in part by the ability of GAPDH to bind TRAF2 which in turn contributes to NF-κB activation and subsequent HIF-1 activation.

GAPDH-Dependent Activation of NF-κB/HIF-1α Leads to CD20 Overexpression in Lymphoma Cells.

Counter intuitively, it was recently suggested that an increase in HIF-1α expression is a favorable prognosis factor in DLBCL patients treated with R-CHOP (Evens et al., 2010). As we observed that GAPDH increases HIF-1α expression in hypoxia, we investigated the overall survival of DLBCL patients for which we previously analyzed mRNA levels of gapdh by qPCR and which were all treated with Rituximab-based chemotherapy upon diagnosis. Strikingly, while 100% of the patients presenting DLBCL with "high" levels of gapdh mRNA were still alive 350 days following the diagnosis, they were only 33% in the "low" gapdh group. Knowing that this HIF-1α-dependent favorable prognosis was observed in R-CHOP but not in CHOP-treated patients (Evens et al., 2010), we investigated the expression of ms4a1 (CD20 encoding gene) and revealed that the "high" gapdh DLBCL samples are presenting more ms4a1 expression than "low" gapdh group. Immunohistochemical analysis of GAPDH and CD20 expression confirmed that a weak expression of GAPDH (shown as a low percentage of positive cells) in DLBCL biospsies (patients #1 and 2) correlates with no/low expression of CD20. In contrast, a high expression of GAPDH (patients #3 and 4) is accompanied with a strong expression of CD20, further underlying the correlation between GAPDH and CD20 expression in patient samples.

To get deeper into the mechanism of CD20 expression, we observed that upon 24 hours of hypoxia, primary Eμ-Myc cells are showing a 2-fold increase in mRNA level of ms4a1 when compared to normoxia. We also established that in vivo inhibition of GAPDH using KA, which led to the inability of GAPDH to bind TRAF2 and to a decrease in hif-1α expression, resulted in a reduction in ms4a1 expression in lymphoma bearing mice. We then confirmed the effects of hypoxia on CD20 cell surface expression using the human Burkitt's lymphoma cell line Raji.

Additional Results

Figure 4:
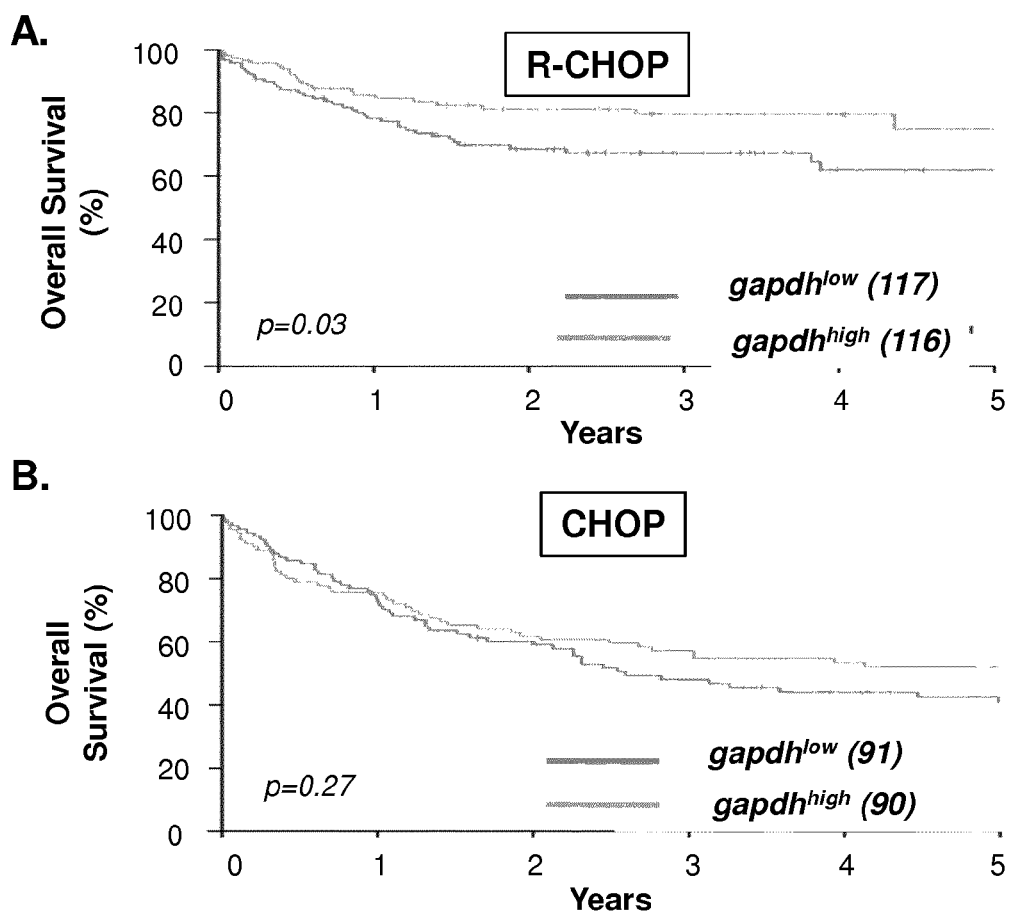
FIG. 4: A. B. Kaplan-Meier curves of overall survival (OS) according to the treatment and the level of gapdh mRNA. (n=117 for gapdh$^{low}$ and n=116 for gapdh$^{high}$ patients in R-CHOP group (A.); n=91 for gapdh$^{low}$ and n=90 for gapdh$^{high}$ patients in CHOP group (B.)).

To extend this observation, we used an extensive primary DLBCL expression profile dataset of 414 patients (Lenz et al, N Engl J Med 2008; 359:2313-2323). As above, we divided R-CHOP-treated patients as "high" and "low" expressers of each glycolytic gene. Similar to initial observations, among 9 glycolytic enzymes (gapdh, hekokinase-2 (hk2), phosphoglucose isomerase (pgi), phosphofructokinase muscle (pfkm), phosphoglycerate kinase-1 (pgk-1), phosphoglycerate mutase-1 (pgam1), enolase-1 (eno1), pyruvate kinase (pk), and lactate dehydrogenase-a (ldh-a), only the gapdh expression level, when elevated, defined a favorable outcome upon R-CHOP treatment (FIG. 4A, p=0.03). Interestingly, gapdh expression did not show any differences in OS for CHOP-treated patients (FIG. 4B).

Discussion

Differences in metabolism were among the first identified variations between normal and cancer cells. Indeed cancer cells have to develop various ways to adapt metabolism to support inappropriate cell proliferation and sustain survival in abnormal tissue context. While most, if not all, glycolytic enzymes are found overexpressed in the vast majorities of cancers (Altenberg and Greulich, 2004), their role in oncogenesis is far from being understood. It was long considered that overexpression of glycolytic enzymes was only required for meeting the energy demand of the cancer cells. However recently non-glycolytic roles of those enzymes are starting to emerge in several settings but rarely in the context of cancers (Chang et al., 2013; Colell et al., 2007; Jacquin et al., 2013; Luo et al., 2011; Majewski et al., 2004; Yang et al., 2011)

Here we provide evidences that GAPDH but not other glycolytic enzymes tested, is a key regulator of c-myc dependent lymphomagenesis. We established that in hypoxic condition, GAPDH binds TRAF2, leading to IκB phosphorylation and NF-κB activation. Several lines of evidences suggested that GAPDH might be involved in the modulation of NF-κB signaling (Bouwmeester et al., 2004; Gao et al., 2013; Mookherjee et al., 2009) but never under hypoxic condition and/or in the context of cancer. We established for the first time that the GAPDH-dependent activation of NF-κB led to an increase in hif-1α transcription both in normoxia and in hypoxia, and of HIF-1α protein expression in hypoxia. Indeed, HIF is a dimer comprised of an α (HIFα) and a β subunit (also known as ARNT). Under hypoxic conditions, its degradation is inhibited, allowing HIFα to accumulate, dimerism with HIFβ, and translocate to the nucleus and activate transcription of HIF-1α target genes. We demonstrated that upon hypoxia, GAPDH lead to HIF-1a induction and to the upregulation of its transcriptional activity. Knowing that GAPDH is one of HIF-1α targeted gene, it underlines the existing positive feedback loop between those proteins.

TRAF2-GAPDH binding is disrupted either upon mutation of key amino-acid involved in GAPDH activity (C152) or by the use of a covalent GAPDH inhibitor, koningic acid. In these conditions, the inability of GAPDH to bind TRAF2 decreased NF-κB activity, reduced HIF-1α expression and correlated closely with the inability of this mutated form to increase lymphomagenesis in vivo, as opposed to the WT form of GAPDH. As it was already suggested upon TNFα stimulation (Gao et al., 2013), we confirmed that C152, cysteine required for the glycolytic function of the enzyme, is essential for GAPDH-TRAF2 binding and for NF-κB/HIF induction. Whether the glycolytic function per se is required still remains unknown as C152 mutation will also impact on the non-glycolytic functions of GAPDH (Colell et al., 2007; Gao et al., 2013; Hara et al., 2005).

It is well established that GAPDH can interact with nucleic acids, for review (Colell et al., 2009). GAPDH was further characterized as an RNA-binding protein, with preference to AU-rich elements, and localized the binding activity to the Rossmann fold of the enzyme (Nagy et al., 2000). GAPDH regulates mRNA stability and consequently controls the expression of proteins, such as endothelin-1 (Rodriguez-Pascual et al., 2008), colony-stimulating factor-1 (CSF-1) (Zhou et al., 2008) or interferon-γ (Chang et al., 2013). Therefore we cannot exclude that on top of GAPDH ability to activate the NF-kB/HIF pathway upon hypoxia, the RNA-binding ability of GAPDH could also contribute in part to stabilize hif-1α and/or vegf-α mRNA.

GAPDH expression upon hypoxia further stimulates vegf-α expression and total VEGF secretion in vivo suggesting that through its ability to induce NF-κB/HIF pathway, GAPDH may play a broader role in cancer progression than has been appreciated before. It is appealing to speculate that some tumors may adopt glycolytic metabolism not only for proliferating but to facilitate their survival.

It was recently suggested that an increase in HIF-1α expression could enhance CD20 expression and represent a favorable marker for DLBCL patients treated with R-CHOP but not with CHOP (Evens et al., 2010). While the majority of reports described that increased HIF-1α expression is associated with increased risk of metastasis and/or inferior survival, the correlation of HIF-1α with improved outcome is not unprecedented (Beasley et al., 2002; Lidgren et al., 2005). These findings hint at the intriguing idea that GAPDH expression by controlling NF-κB/HIF signaling is a central regulator of CD20 expression. Indeed, we established that increased GAPDH expression correlates with an increased CD20 expression in patients' biopsies and that GAPDH inhibition prevents its binding to TRAF2 and reduces ms4a1 (CD20 gene) expression and cell surface expression of CD20 upon hypoxia. Furthermore we found that patients with DLBCL treated with R-CHOP had superior outcome if GAPDH was highly expressed. Finally, we established that CD20 was over-expressed upon hypoxia in a GAPDH and HIF-1α dependent manner. Interestingly among the identified regulatory factors involved in a positive regulation of CD20 there is IRF4/PU.1 (Himmelmann et al., 1997), two characterized targets of NF-κB (Bonadies et al., 2010; Grumont and Gerondakis, 2000). Consequently, combined evidences of the literature suggest that activation of NF-κB through GAPDH could participate in the transcriptional control of CD20.

Downregulation of CD20 has been observed in a number of case reports of patients with relapsed/refractory B-cell lymphoma who became unresponsive to rituximab-based therapies and has been postulated to be one of the most important etiologies contributing to rituximab resistance (Haidar et al., 2003; Jilani et al., 2003). We could speculate that modification of GAPDH expression associated with a modification of tumor cell metabolism over treatment could participate in the down regulation of the expression of CD20.

Using pre-clinical models and clinical samples of NH-lymphomas we established that GAPDH has a dual role in myc-induced lymphomagenesis, while increasing tumor aggressiveness and vascularization, it enhances CD20 expression and increases the patient's response to anti-CD20 based treatment. As c-Myc is found up regulated in about <70% of all human tumors and as GAPDH is widely overexpressed in most tumor types, our observation is more broadly relevant to other types of cancers.

Experimental Procedures

Stable Transgenic Cells

GAPDH overexpressing HeLa cells were infected as previously described (Colell et al., 2007). Transduction of primary Eμ-Myc cells was made as previously described (Beneteau et al., 2012). One week after transduction, infected cell populations were sorted by flow cytometer BD Aria for GFP positive cells and expression of protein of interest was assessed by immunoblotting.

Co-Immunoprecipitation

Protein G Sepharose 4B beads (Invitrogen, CA, USA) were first incubated with rabbit anti-TRAF2 or mouse anti-GAPDH antibody or IgG control (Santacruz, Calif., USA) for 4 hours at 4° C. Beads were then incubated overnight with 1 mg of precleared protein lysed in 20 mM Tris-HCl, pH 7.4, 137 mM NaCl, 1 mM EGTA, 10% glycerol, 1% Triton X-100, 1.5 mM $MgCl_2$, 1 μg/μl PMSF, protease and phosphatase inhibitor cocktail (Thermo Scientific). Samples were then washed five times, boiled in Laemmli buffer and analyzed by immunoblotting with the indicated antibodies Staining for CD20 Expression Cells ($0.5 \cdot 10^6$) cells (in triplicate) were washed 1×PBS and incubated at 4° C. with the monoclonal anti-CD20 (Affymetrix eBioscience) at a concentration of 2.5 μg/ml for 45 minutes. IgG isotypic controls were included. Cells were then washed 2×PBS and incubated at 4° C. for 30 minutes in the dark with a anti-mouse Alexa 488 (1 μg/ml). Then cells were washed twice in PBS and resuspend in 100 μl of PBS containing 0.5 μg/ml of DAPI (4',6-diamidino-2-phenylindole). Ten thousand events were analyzed immediately by flow cytometry using a MACSQuant Analyzer (Miltenyi Biotec). The mean fluorescence intensity (MFI) obtained for lived (DAPI negative) CD20 positive cells was reported. Histograms represent the average of three independent experiments.

Transgenic Mice, Transplantation of Lymphomas and Lymph Nodes Analysis.

All mice were maintained in specific pathogen-free conditions and experimental procedures were approved by the Institutional Animal Care and Use Committee and by the regional ethics committee (NCE/2011-35 from Comite Institutionnel d'Ethique Pour l'Animal de Laboratoire—AZUR). C57BL/6 Eμ-Myc transgenic mice were purchased from the Jackson Laboratory. Lymphoma-bearing animals were killed by cervical dislocation as soon as they presented sign of suffering. Eμ-Myc cells were obtained and used as described previously (Beneteau et al., 2012). The first signs of the pathology were determined by inguinal lymph node palpation and analyses of blood sample with Hemavet 950FS (Drew Scientific, INC, France). Upon sacrifice all lymph node tumors are immediately collected and weighted before freezing or analyzing by FACS for alive CD19 and GFP positive cells. Frozen lymph node tumors embedded in OCT (Thermoelectron Corp) were subjected to immunofluorescence for CD31 expression. Frozen tumor tissues were lysed in cell extraction buffer (Promega). The intra-tumor hemoglobin content was measured by using the Drabkin reagent kit 525 (Sigma). Total mouse or human VEGF was measured by using PeproTech ELISA kits according to the manufacturer's recommandations.

Patients and Tissue Sample Preparation

Thirteen patients who underwent biopsy for DLBCL between May 2007 and May 2011 at the Saint-Louis Hospital (Department of Onco-hematology, Hopital Saint-Louis, Paris, France) were selected. The patients received the necessary information concerning the study and consent was obtained. Morphologic classification of the tumors was assigned according to the World Health Organization (WHO) criteria (Campo et al., 2011). The tumors extensions were staged according to the Ann Arbor stage, and all patients were scored by IPIaa (project, 1993). Follow-up data for all the patients were collected regularly. Among these patients, 8 relapsed (61.5%) and 6 (46%) died.

Immunohistochemistry

Section (3 μm) of formalin-fixed, paraffin-embedded DLBCL biopsies were treated using standard procedures and immunostained automatically (Ventana) for GAPDH (Prestige, Sigma, 1/400), CD20 (1/800 clone L26 DAKO) and CD79A (1/100 clone JCB117 Dako) expressions.

Statistical Analysis

Data are expressed as mean±standard deviation (SD). Differences in the calculated mean between each group were analyzed using Fisher test (quantitative variable). Survival functions were estimated by the Kaplan-Meier method and compared by the log-rank test. A P value of 0.05 or less was considered to indicate statistical significance. Kaplan-Meier survival curves and box plot representations were performed using "R" software.

Progression Free survival (PFS) was measured from the date of diagnosis to that of death from any cause or to the stopping date. When the latter date was not reached, the data were censored at the date of the last follow-up evaluation. Continuous biologic variables were dichotomized by applying the standard split-sample approach. The resulting thresholds were checked by including cubic smoothing splines in the risk function of the Cox model. Spline curve was used to determine the best cut-off point to discriminate the DBCL "low" and "high" expressers of gapdh.

Cell Culture and Hypoxic Exposure

HeLa and Raji cells were obtained from ATCC and cultured as recommended. Mouse primary Eμ-Myc lymphoma (B lymphoma cells) were isolated as described previously (Lindemann et al., 2007) and maintained in DMEM supplemented with 10% FCS, 2-mercaptoethanol (50 μM), L-asparagin (0.37 mM) and HEPES (pH 7.4, 10 mM). Incubation in hypoxia at 1% $O_2$ was carried out at 37° C. in 95% humidity and 5% $CO_2$/94% $N_2$ in a sealed anaerobic workstation (Whitley hypoxystation H35).

Reagents and Antibodies

Mouse anti-V5 was purchased from Invitrogen (Carlsbad, Calif., USA), rabbit anti-GAPDH was purchased from (Abcam), mouse anti-Erk2 was purchased from Santa Cruz Biotechnology (Santa Cruz, Calif., USA). Rabbit anti-GAPDH used for immunohistochemistry was a "Prestige antibody" purchased from Sigma. Mouse anti-GAPDH used for immunoprecipitation was purchased from Santa Cruz Biotechnology. Rabbit anti-HIF-1α was prepared and validated in Dr. J. Pouysségur's laboratory. Anti-CD19-PE was purchased from BD Bioscience. Monoclonal anti-CD20 was purchased from Affymetrix eBioscience. Anti-CD31 was purchased from BD Pharmigen. Other antibodies were purchased from Cell Signaling Technology (Beverly, Mass., USA). GAPDH specific inhibitor, Koningic acid (KA) was purchased from Euromedex.

Measurement of GAPDH Activity

Cells were lysed in a buffer containing 10 mmol/L HEPES (pH 7.4), 150 mmol/L NaCl, 5 mmol/L EDTA, 1% NP40, 10 μg/mL aprotinin, 1 mmol/L phenylmethylsulfonyl fluoride and 10 mmol/L leupeptin (buffer A). Lysates were standardized for protein content and incubated with 0.25 mmol/L NAD, 3.3 mmol/L DTT, 13 mmol/L $Na_4P_2O_7$ (pH 8.5), 26 mmol/L sodium arsenate, and 25 mmol/L D-glyceraldehyde-3-phosphate in a black 96-well plate (Cellstar). GAPDH activity was measured on a fluoroscan at 445 nm as the increase in fluorescence related to NADH accumulation. Activity is expressed as the change in absorbance per milligram of protein.

Plasmids

Full-length human gapdh (GAPDH-V5) and gapdh double mutant GAPDHC152S/H179F-V5 (DM-V5) cDNA were obtained and inserted into the pcDNA™3.1/V5-His TOPO® TA expression plasmid (Invitrogen) as previously described (Colell et al., 2007). Using a cDNA library and following classical methods, Enolase 1 (NP_001419), PKM2 (NP_872270) were cloned by PCR in the pcDNA™3.1/V5-His TOPO® TA expression plasmid (Invitrogen) and Bcl-xL (NP_001182) was cloned in pcDNA3. GAPDH, DM, ENOL, PKM2, Bcl-xL were then subcloned in a pMIG-GFP viral vector for retroviral infection.

Complementary sense and antisense oligonucleotides were annealed and into BglII/HindIII-cut pSUPER retro.Neo+GFP vector (oligoengine). shRNA targeting luciferase was used as a control shRNA (shctl) (Beneteau et al., 2012), excepted for luciferase assay (empty pSUPER retro.Neo+GFP vector was used).

RNA Extraction and Real-Time Quantitative PCR

Total RNA was extracted from cells using the RNA extraction kit (Qiagen) according to the manufacturer's instructions. Total RNA (2 μg) was added to 20 μl reverse transcription-PCR using the Omniscript kit (Qiagen). The relative mRNA expression level of gapdh, hif-1α, ca9, vegf-α, ldh-a (mouse and human) were obtained by real-time quantification PCR (qPCR), using the TaqMan PCR Master Mix (Eurogentec) and TaqMan assay primer set (Applied Biosystems, Foster City, Calif.) on the 7500 Fast and the Step One (Applied Biosystems) according to the manufacturer's instructions (sequences provided upon request). For in vitro experiment, all samples were normalized to rplp0. All mRNA samples from human tumor tissues were normalized by ppia (cyclophilin-a).

Western Blot Analysis

Briefly, after exposure to normoxia or hypoxia, cells were washed and lysed in laemmli buffer. Cells exposed to hypoxia were lysed in the hypoxic chamber. Proteins (40 μg) were separated on 8% to 12% SDS polyacrilamide gels and transferred onto polyvinylidene difluoride membranes (Millipore). Membranes were then blotted with antibody corresponding to the indicated proteins. Immunoreactive bands were detected with a horseradish peroxidase (HRP) anti-mouse (Dako) or anti-rabbit (Cell Signaling) by enhanced chemiluminescence (Pierce). When indicated, Western blot quantification was made using ImageJ software.

Determination of the Rate of Glycolysis.

In vitro. The lactate exported in the supernatant of cells incubated either in normoxia (N) or in hypoxia of 1% $O_2$ (Hx) for 1, 3, 6, 9, hours in a pyruvate-free DMEM was determined by an enzyme-based assay using 900 μM β-NAD (BioChemika), 175 μg/mL L-lactate dehydrogenase (BioChemika), and 100 μg/mL glutamate-pyruvate transaminase (Roche) diluted in a sodium carbonate (620 mM)-L-gultamate (79 mM) buffer adjusted to pH 10. Lithium lactate was used as a standard.

In Vivo. Intact Lymph nodes were dissociated in a lysis buffer A. Lactate concentration was determined as described and normalized by the total protein quantity.

Proliferation Assays

HeLa cells ($1 \times 10^5$) were seeded in 100 mm dish. The cells were detached and counted 24 hours after seeding and every 24 hours during 3 days. Eμ-Myc cells ($4 \times 10^5$ cells/ml) were seeded in T-25 $cm^2$ flask and counted every day for 3 days. The proliferation index was calculated by dividing the cell number obtained for each day by the one obtained 24 hours after seeding.

Luciferase Assays

HIF-1 activity. HeLa cells stably expressing the p3HRE-Dptk-LUC vector, which contain three copies of the hypoxia-responsive element (HRE) from the erythropoietin gene (Dayan et al., 2006), were transiently transfected (calcium phosphate) with control vector (pMIG or empty pSUPER vector) or vectors (2 μg) to either overexpress or to silence GAPDH. The following day, transfected cells were exposed to normoxia or hypoxia 1% $O_2$ for 24 hours before cell lysis in a reporter lysis buffer (Promega). It is worth noting that for determination of HIF-1 activity in hypoxia, cells were directly lysed in the hypoxic chamber). The luciferase assay was performed as previously described (Jacquin et al., 2013).

NF-κB Activity.

HeLa cells stably expressing GAPDH-V5 or GAPDH double mutant (DM-V5) control (pMIG) were transiently co-transfected by the classical calcium phosphate method with 0.5 μg of a vector encoding cFP and 2 μg of a luciferase reporter gene controlled by a minimal tk promoter ans sex reiterated KB sites (icBx6 tk luc). Forty-eight hours after transfection, cells were exposed to either normoxia or hypoxia 1% $O_2$ for 24 hours before harvesting and analyzing as previously described (Bottero et al., 2003).

Electrophoretic Mobility Shift Assay (EMSA)

Total cell extracts from Raji cells treated or not with 0.2 μg/ml of KA and exposed to normoxia or hypoxia 1% $O_2$ for 24 hours were prepared as previously described (Bottero et al., 2003). For mobility shift assay, a NF-κB probe consisting of a synthetic double stranded oligonucleotide containing the KB binding site of the Igκ promoter was used. The end-labeled probe (T4 kinase) was incubated with extracts samples for 20 minutes at 30° C. Complexes were separated by electrophoresis on a 5% non-denaturating polyacrylamide gel in 0.5×TBE. Dried gels were subjected to autoradiography.

Immunofluorescence of CD31

Frozen lymph node tumors embedded in OCT (Thermoelectron Corp) were subjected to immuno fluorescence for CD31 expression (see supplemental material). cut at −20° C. (Cryostat, Leica) and 5 μm slides were then fixed in aceton for 20 min at −20° C., washed, saturated and stained with rat anti-CD31 (2.5 μg/ml) overnight at 4° C. in a humidified chamber. After incubation, coverslips were washed and incubated for 1 h at room temperature with DAPI (1 μg/ml) and an anti-rat Alexa 488 (2 μg/ml) in the dark. Tumor slides were mounted with fluoromount G and analyzed with a confocal microscope (LSM 510 Meta Zeiss).

Example 2

Methods and Material
Reagents

For FACS staining: Anti-GAPDH (Abcam), -CD20-FITC (clone L26, eBioscience) were used. Koningic acid (KA) was purchased from Euromedex.

Cell Culture and Hypoxic Exposure

Raji cells (human Burkitt NH B lymphoma cell line) were obtained from ATCC and cultured as recommended. RL cells (human Follicular NH B lymphoma cell line) were obtained from Pr. Charles Dumontet and cultured as described (Dalle S et al, Clin Cancer Res, 2009, 15(3):851-7). Incubation in hypoxia was carried out at 1% $O_2$ (as opposed to normoxic, 21% $O_2$ incubation), 37° C. in 95% humidity and 5% $CO_2$/94% $N_2$ in a sealed anaerobic workstation (Whitley hypoxystation H35).

Staining for CD20 and GAPDH Expression

A total of $1 \times 10^6$ cells were washed in PBS and incubated for 45 minutes at 4° C. with the monoclonal anti-CD20 antibody (2.5 µg/ml) (Affymetrix eBioscience). The cells were then washed in PBS and incubated at 4° C. for 30 minutes with an anti-mouse Alexa Fluor 488 (1 µg/ml). Cells are permeabilized and fixed using the BD Cytofix/cytoperm solution (BD Biosciences) and incubated at 4° C. for 20 min. The cells are then washed in saponin containing buffer (BD Perm/Wash) and resuspended in the same buffer containing anti-GAPDH antibody (Abcam ab9485; dilution 1/100) and incubated for 30 min at 4° C. The cells are washed twice with the saponin-containing buffer and incubated with a APC-coupled anti-Rabbit antibody (dilution 1/100) for 30 min at 4° C. in the same buffer. After washing twice in the saponine-containing buffer, the cells are resuspended in PBS/2% FCS and analyzed by flow cytometry. Immediately afterwards, 10,000 events were analyzed by flow cytometry using a MACSQuant Analyzer (Miltenyi Biotec). The mean fluorescence intensity (MFI) obtained for CD20-low, CD20-high, GAPDH-low, GAPDH-high cells, was reported.

Microarray Data Analysis

Raw data (GSE10846) were normalized and log 2 transformed using the justRMA function (affy package). When a gene was represented by several probesets, the median intensity was used. Survival curves were plotted following the Kaplan-Meier method using the median value as the cut-off point, and hazard ratios were obtained using Cox regression.

Results

Figure 2:
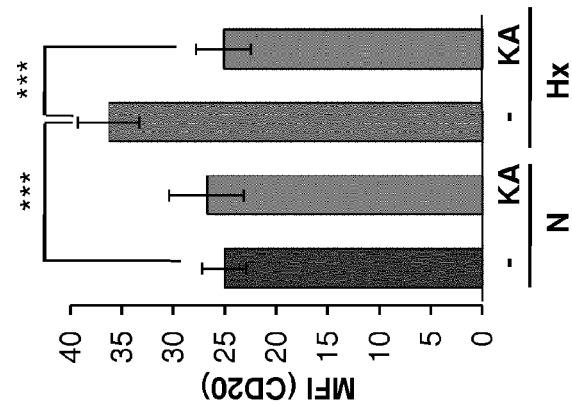
FIG. 2. A. GAPDH expression in Burkitt lymphoma cell line (Raji cells) incubated in normoxia (21% $O_2$) or in hypoxia (1% $O_2$) for 24 hours. B. Left: Representative histogram overlays of the effect obtained on CD20 cell surface expression after 48 hours of normoxic (N) or hypoxic 1% $O_2$ (Hx) incubation of live Burkitt lymphoma Raji cells. Right: Quantification of the mean of fluorescence intensity (CD20) on live Raji cells treated (KA) or not (−; DMSO) with GAPDH inhibitor KA (0.1 µg/ml) and exposed to normoxia or hypoxia for 48 h.
Figure 2:
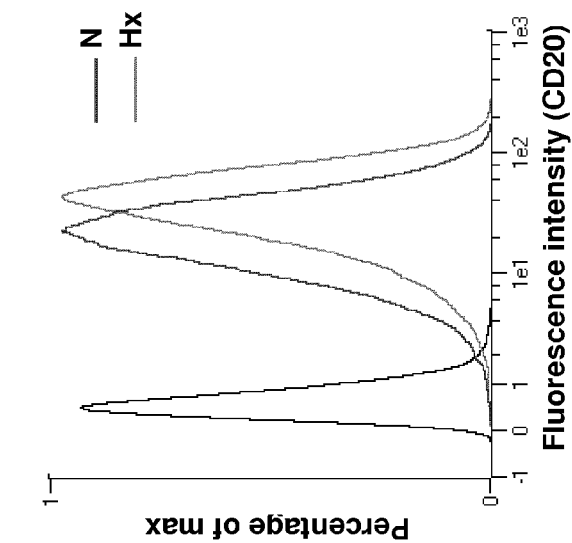
Figure 2:
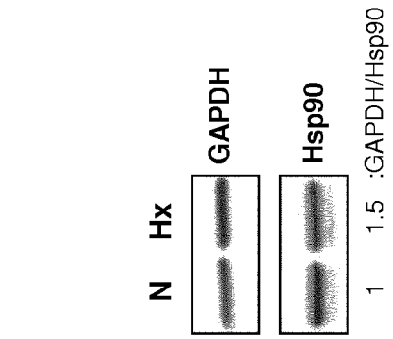
Figure 3:
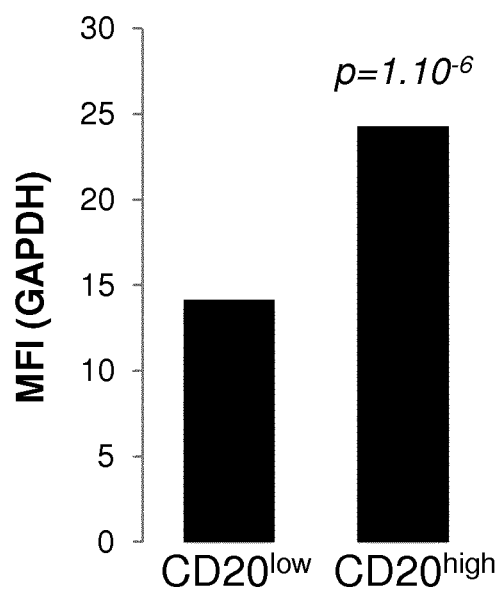
FIG. 3. CD20 cell surface expression and GAPDH intracellular expression determined by FACS (mean fluorescence intensity) in human follicular lymphoma RL cell line.

We also demonstrated the relationship between CD20 and GAPDH expression in two other NH B lymphomas such as Burkitt and Follicular lymphomas (FIGS. 2 and 3). For human Burkitt NH-lymphoma, Raji cell line was incubated under hypoxia to physiologically increase GAPDH expression (FIG. 2A). CD20 cell surface expression was increased in the Raji cells exposed to hypoxia (FIG. 3B), a process mediated though GAPDH activity, as specific GAPDH inhibition using non-toxic doses of koningic acid prevented this hypoxic-dependent increase in CD20 expression. For human follicular lymphoma, low levels of CD20 expression at the cell surface correlate with a low expression of intracellular GAPDH in RL cell line. In contrast, high level of CD20 is associated with a high level of GAPDH expression in this model (FIG. 3).

REFERENCES

Throughout this application, various references describe the state of the art to which this invention pertains. The disclosures of these references are hereby incorporated by reference into the present disclosure.

Alizadeh, A. A., Eisen, M. B., Davis, R. E., Ma, C., Lossos, I. S., Rosenwald, A., Boldrick, J. C., Sabet, H., Tran, T., Yu, X., et al. (2000). Distinct types of diffuse large B-cell lymphoma identified by gene expression profiling. Nature 403, 503-511.

Altenberg, B., and Greulich, K. O. (2004). Genes of glycolysis are ubiquitously overexpressed in 24 cancer classes. Genomics 84, 1014-1020.

Beasley, N. J., Leek, R., Alam, M., Turley, H., Cox, G. J., Gatter, K., Millard, P., Fuggle, S., and Harris, A. L. (2002). Hypoxia-inducible factors HIF-1alpha and HIF-2alpha in head and neck cancer: relationship to tumor biology and treatment outcome in surgically resected patients. Cancer Res 62, 2493-2497.

Beneteau, M., Zunino, B., Jacquin, M. A., Meynet, O., Chiche, J., Pradelli, L. A., Marchetti, S., Cornille, A., Carles, M., and Ricci, J. E. (2012). Combination of glycolysis inhibition with chemotherapy results in an antitumor immune response. Proc Natl Acad Sci USA 109, 20071-20076.

Bonadies, N., Neururer, C., Steege, A., Vallabhapurapu, S., Pabst, T., and Mueller, B. U. (2010). PU.1 is regulated by NF-kappaB through a novel binding site in a 17 kb upstream enhancer element. Oncogene 29, 1062-1072.

Bottero, V., Imbert, V., Frelin, C., Formento, J. L., and Peyron, J. F. (2003). Monitoring NF-kappa B transactivation potential via real-time PCR quantification of I kappa B-alpha gene expression. Molecular diagnosis: a journal devoted to the understanding of human disease through the clinical application of molecular biology 7, 187-194.

Bouwmeester, T., Bauch, A., Ruffner, H., Angrand, P. O., Bergamini, G., Croughton, K., Cruciat, C., Eberhard, D., Gagneur, J., Ghidelli, S., et al. (2004). A physical and functional map of the human TNF-alpha/NF-kappa B signal transduction pathway. Nature cell biology 6, 97-105.

Campo, E., Swerdlow, S. H., Harris, N. L., Pileri, S., Stein, H., and Jaffe, E. S. (2011). The 2008 WHO classification of lymphoid neoplasms and beyond: evolving concepts and practical applications. Blood 117, 5019-5032.

Chang, C. H., Curtis, J. D., Maggi, L. B., Jr., Faubert, B., Villarino, A. V., O'Sullivan, D., Huang, S. C., van der Windt, G. J., Blagih, J., Qiu, J., et al. (2013). Posttranscriptional control of T cell effector function by aerobic glycolysis. Cell 153, 1239-1251.

Colell, A., Green, D. R., and Ricci, J. E. (2009). Novel roles for GAPDH in cell death and carcinogenesis. Cell Death Differ 16, 1573-1581.

Colell, A., Ricci, J. E., Tait, S., Milasta, S., Maurer, U., Bouchier-Hayes, L., Fitzgerald, P., Guio-Carrion, A., Waterhouse, N. J., Li, C. W., et al. (2007). GAPDH and autophagy preserve survival after apoptotic cytochrome c release in the absence of caspase activation. Cell 129, 983-997.

Dayan, F., Roux, D., Brahimi-Horn, M. C., Pouyssegur, J., and Mazure, N. M. (2006). The oxygen sensor factor-inhibiting hypoxia-inducible factor-1 controls expression of distinct genes through the bifunctional transcriptional character of hypoxia-inducible factor-1alpha. Cancer Res 66, 3688-3698.

Evens, A. M., Sehn, L. H., Farinha, P., Nelson, B. P., Raji, A., Lu, Y., Brakman, A., Parimi, V., Winter, J. N., Schumacker, P. T., et al. (2010). Hypoxia-inducible factor-1 {alpha} expression predicts superior survival in patients with diffuse large B-cell lymphoma treated with R-CHOP. J Clin Oncol 28, 1017-1024.

Gao, X., Wang, X., Pham, T. H., Feuerbacher, L. A., Lubos, M. L., Huang, M., Olsen, R., Mushegian, A., Slawson, C., and Hardwidge, P. R. (2013). NleB, a bacterial effector with glycosyltransferase activity, targets GAPDH function to inhibit NF-kappaB activation. Cell host & microbe 13, 87-99.

Grumont, R. J., and Gerondakis, S. (2000). Rel induces interferon regulatory factor 4 (IRF-4) expression in lymphocytes: modulation of interferon-regulated gene expression by rel/nuclear factor kappaB. The Journal of experimental medicine 191, 1281-1292.

Haidar, J. H., Shamseddine, A., Salem, Z., Mrad, Y. A., Nasr, M. R., Zaatari, G., and Bazarbachi, A. (2003). Loss of CD20 expression in relapsed lymphomas after rituximab therapy. European journal of haematology 70, 330-332.

Hara, M. R., Agrawal, N., Kim, S. F., Cascio, M. B., Fujimuro, M., Ozeki, Y., Takahashi, M., Cheah, J. H., Tankou, S. K., Hester, L. D., et al. (2005). S-nitrosylated GAPDH initiates apoptotic cell death by nuclear translocation following Siahl binding. Nature cell biology 7, 665-674.

Harris, A. W., Pinkert, C. A., Crawford, M., Langdon, W. Y., Brinster, R. L., and Adams, J. M. (1988). The E mu-myc transgenic mouse. A model for high-incidence spontaneous lymphoma and leukemia of early B cells. The Journal of experimental medicine 167, 353-371.

Himmelmann, A., Riva, A., Wilson, G. L., Lucas, B. P., Thevenin, C., and Kehrl, J. H. (1997). PU.1/Pip and basic helix loop helix zipper transcription factors interact with binding sites in the CD20 promoter to help confer lineage- and stage-specific expression of CD20 in B lymphocytes. Blood 90, 3984-3995.

Jacquin, M. A., Chiche, J., Zunino, B., Beneteau, M., Meynet, O., Pradelli, L. A., Marchetti, S., Cornille, A., Carles, M., and Ricci, J. E. (2013). GAPDH binds to active Akt, leading to Bcl-xL increase and escape from caspase-independent cell death. Cell Death Differ 20, 1043-1054.

Jilani, I., O'Brien, S., Manshuri, T., Thomas, D. A., Thomazy, V. A., Imam, M., Naeem, S., Verstovsek, S., Kantarjian, H., Giles, F., et al. (2003). Transient downmodulation of CD20 by rituximab in patients with chronic lymphocytic leukemia. Blood 102, 3514-3520.

Lidgren, A., Hedberg, Y., Grankvist, K., Rasmuson, T., Vasko, J., and Ljungberg, B. (2005). The expression of hypoxia-inducible factor 1alpha is a favorable independent prognostic factor in renal cell carcinoma. Clin Cancer Res 11, 1129-1135.

Lindemann, R. K., Newbold, A., Whitecross, K. F., Cluse, L. A., Frew, A. J., Ellis, L., Williams, S., Wiegmans, A. P., Dear, A. E., Scott, C. L., et al. (2007). Analysis of the apoptotic and therapeutic activities of histone deacetylase inhibitors by using a mouse model of B cell lymphoma. Proc Natl Acad Sci USA 104, 8071-8076.

Luo, W., Hu, H., Chang, R., Zhong, J., Knabel, M., O'meally, R., Cole, Robert N., Pandey, A., and Semenza, Gregg L. (2011). Pyruvate Kinase M2 Is a PHD3-Stimulated Coactivator for Hypoxia-Inducible Factor 1. In Cell, pp. 732-744.

Majewski, N., Nogueira, V., Bhaskar, P., Coy, P. E., Skeen, J. E., Gottlob, K., Chandel, N. S., Thompson, C. B., Robey, R. B., and Hay, N. (2004). Hexokinase-mitochondria interaction mediated by Akt is required to inhibit apoptosis in the presence or absence of Bax and Bak. Mol Cell 16, 819-830.

Mookherjee, N., Lippert, D. N., Hamill, P., Falsafi, R., Nijnik, A., Kindrachuk, J., Pistolic, J., Gardy, J., Miri, P., Naseer, M., et al. (2009). Intracellular receptor for human host defense peptide LL-37 in monocytes. J Immunol 183, 2688-2696.

Nagy, E., Henics, T., Eckert, M., Miseta, A., Lightowlers, R. N., and Kellermayer, M. (2000). Identification of the NAD(+)-binding fold of glyceraldehyde-3-phosphate dehydrogenase as a novel RNA-binding domain. Biochemical and biophysical research communications 275, 253-260.

project, T. I. N.-H. s. 1. p. f. (1993). A predictive model for aggressive non-Hodgkin's lymphoma. N Engl J Med 329, 987-994.

Rodriguez-Pascual, F., Redondo-Horcajo, M., Magan-Marchal, N., Lagares, D., Martinez-Ruiz, A., Kleinert, H., and Lamas, S. (2008). Glyceraldehyde-3-phosphate dehydrogenase regulates endothelin-1 expression by a novel, redox-sensitive mechanism involving mRNA stability. Mol Cell Biol 28, 7139-7155.

Thieblemont, C., and Gisselbrecht, C. (2009). Second-line treatment paradigms for diffuse large B-cell lymphomas. Current oncology reports 11, 386-393.

Tsai, P. C., Hernandez-Ilizaliturri, F. J., Bangia, N., Olejniczak, S. H., and Czuczman, M. S. (2012). Regulation of CD20 in rituximab-resistant cell lines and B-cell non-Hodgkin lymphoma. Clin Cancer Res 18, 1039-1050.

Yang, W., Xia, Y., Ji, H., Zheng, Y., Liang, J., Huang, W., Gao, X., Aldape, K., and Lu, Z. (2011). Nuclear PKM2 regulates beta-catenin transactivation upon EGFR activation. Nature 480, 118-122.

Zhou, Y., Yi, X., Stoffer, J. B., Bonafe, N., Gilmore-Hebert, M., McAlpine, J., and Chambers, S. K. (2008). The multifunctional protein glyceraldehyde-3-phosphate dehydrogenase is both regulated and controls colony-stimulating factor-1 messenger RNA stability in ovarian cancer. Mol Cancer Res 6, 1375-1384.

The invention claimed is:

1. A method for treating a patient having non Hodgkin's B cell lymphoma wherein the non Hodgkin's B cell lymphoma is diffuse large B-cell lymphoma, said method comprising the steps of:
   a) identifying a responder patient having diffuse large B-cell lymphoma that is responsive to treatment with an anti human CD20 antibody by measuring a level of glyceraldehyde-3-phosphate dehydrogenase (GAPDH) expression in tumor B-cells obtained from said patient, wherein a high level of GAPDH expression is predictive of a response to said anti-CD20 antibody treatment; and
   b) treating with said anti-CD20 antibody the responder patient identified.

2. The method according to claim 1, wherein the anti-CD20 antibody is selected from the group consisting of rituximab, ibritumomab, ofatumumab, ocrelizumab, PRO131921, veltuzumab, AME-133v, tositumomab, and GA-101.

3. The method according to claim 1, wherein the anti-CD20 antibody is rituximab.

* * * * *